United States Patent
Saccomanno (10) Patent No.: US 6,936,828 B2
(45) Date of Patent: Aug. 30, 2005

(54) PARTICLE DETECTION SYSTEM AND METHOD

(75) Inventor: Robert J. Saccomanno, Montville, NJ (US)

(73) Assignee: Honeywell International Inc., Morristown, NJ (US)

( * ) Notice: Subject to any disclaimer, the term of this patent is extended or adjusted under 35 U.S.C. 154(b) by 230 days.

(21) Appl. No.: 10/367,331

(22) Filed: Feb. 14, 2003

(65) Prior Publication Data

US 2004/0159799 A1 Aug. 19, 2004

(51) Int. Cl.[7] .............................................. G01N 21/64
(52) U.S. Cl. ................................................... 250/458.1
(58) Field of Search ........................ 250/458.1, 459.1, 250/461.1, 461.2

(56) References Cited

U.S. PATENT DOCUMENTS

| | | |
|---|---|---|
| 4,651,010 A | 3/1987 | Javan |
| 4,893,928 A | 1/1990 | Knollenberg |
| 5,561,515 A | 10/1996 | Hairston et al. |
| 5,684,587 A | 11/1997 | Naqwi |
| 5,701,012 A | 12/1997 | Ho |
| 5,876,960 A | 3/1999 | Rosen |
| 5,895,922 A | 4/1999 | Ho |
| 5,999,250 A | 12/1999 | Hairston et al. |
| 6,016,195 A | 1/2000 | Peters |
| 6,118,532 A | 9/2000 | Peters |
| 6,165,740 A | 12/2000 | Fukuda et al. |
| 6,428,198 B1 | 8/2002 | Saccomanno et al. |
| 2002/0118362 A1 | 8/2002 | Seccomanno |
| 2004/0057050 A1 * | 3/2004 | Beck et al. .................. 356/336 |

FOREIGN PATENT DOCUMENTS

WO    WO 9834094 A1    8/1998

OTHER PUBLICATIONS

Hamamatsu Photonics " Si APD S5343, S5344, S5345". Mar. 2001.
Vishay Semiconductor, "Silicon PN Photodiode", Document No. 81519, Rev. 2, May 20, 1999.
Hamamatsu Photonics, "Characteristics and use of Si APD (Avalanche Photodiode)", Jul., 2001.
Hamamatsu Photonics, "Si Photodiode array S4111/S4114 Series," Mar. 2001.
Kartin Kneipp, "Basics of single molecule experiments under ambient conditions," M.I.T. Course 6.975, Spring, 2001.
Hamamatsu Photonics, "Multianode PMT With Band Pass Filters R5900F–L16 Series", Apr., 2000.
Roithner Lasertechnik, "RLT370–10 Technical Data", Undated.

(Continued)

*Primary Examiner*—Constantine Hannaher
(74) *Attorney, Agent, or Firm*—Kurt Luther; Lawrence Eisen (57) ABSTRACT

An apparatus and method for detecting particles. A flow tube is surrounded by eight off-axis ellipsoidal mirrors all having a common first focus coincident with a portion of the flow tube and each having a distinct second focus. In one embodiment, sources of radiation are arranged coincident with exit ports in the mirrors that are also coincident with the respective distinct second foci. These radiation sources are momentarily energized in sequence (or simultaneously), causing light to illuminate a corresponding ellipsoidal mirror. This light strikes the common first focus within a portion of the flow tube. Any particles within the first focus will then scatter the light, and depending upon the source wavelength and the particle, may also provide some amount of fluorescence. This energy is captured by detectors and analyzed to determine the type, size and quantity of particles at the first focus.

37 Claims, 9 Drawing Sheets

OTHER PUBLICATIONS

CREE, G–SiC® Technology MegaBright LEDs CXXX–MB290–EXXX, Undated.

Hamamatsu Photonics, "Xenon Flash Lamps", Apr., 1999.

Particle Instruments Group, Prof. Paul Kaye, "Aerosol Characterization Research at the University of Hertfordshire", Sep., 1998.

Gang Chen et al., "Aerosol fluorescence spectruro analyzer for individual airborne biological particles", SPIE vol. 3105, 1997 pp 378–386.

Yong–le Pan et al., "Single–shot fluorescence spectra of individual micrometer–sized bioaerosols illuminated by a 351—or a 266–nm ultraviolet laser", Optics Letters/vol. 24, No. 2, Jan. 15, 1999 pp 116–118.

Judith R. Mourant et al., "Mechanisms of light scattering from biological cells relevant to noninvasive optical–tissue diagnostics", Applied Optics/vol. 37, No. 16, Jun. 1, 1998 pp 3586–3593.

Yong–le Pan et al., "High–speed, high–sensitivity aerosol fluorescence spectrum detection using a 32–anode photo multiplier tube detector," Review of Scientific Instruments, vol. 72, No. 3, Mar., 2001 pp 1831–1836.

TSI Incorporated, "Model 3312 Ultraviolet Aerodynamic Particle Sizer Spectrometer", Copyright 1997.

M.L. Thatcher et al., "A Rapid Protein Particle Size Measurement Method for Metered Dose Inhaler Development: Novel Use of the Small Scale Powder Disperser and Aerodynamic Particle Sizer®," 3M Drug Delivery Systems, Undated.

Stephen W. Stein et al., "Evaluation of a New Aerodynamic Particle Sizer® Spectrometer for MIDI Size Distribution Measurements", 3M Drug Delivery Systems, Undated.

United States Army Medical Research and Materiel Command, Department of Defense Board Agency Announcement, "BAA 99–1", Dec. 1998.

Internaitonal Search Report; PCT/US2004/004200; Jul. 9, 2004 not a publication.

\* cited by examiner

PARTICLE DETECTION SYSTEM AND METHOD

BACKGROUND

1. Field of the Invention

The present invention relates to systems and methods for detecting and classifying particles through optical means.

2. Background of the Invention

It has been a longstanding desire to provide systems and methods for accurately detecting particle size, quantities, and whether the particles are biological or not. The detection and categorization of biological particles, in particular, is generally referred to as cytometry. Accurate and portable cytometry equipment is presently of critical importance to detect biological pathogens, such as anthrax, or other pathogens that may impact public health.

Known cytometry methodologies make use of fluorescence, often initiated by laser light, to identify particles. In this particular methodology, a laser wavelength is selected to be near or at the peak of an absorption resonance in the particle, trace gas, compound or chemical element to be detected. This absorption resonance is selected to be one that causes strong fluorescence. In one such known cytometry system, described in U.S. Pat. No. 4,651,010 to Javan, laser light illuminates air drawn through a duct, which may bear the particles to be detected, such light having a wavelength near or at the peak of an absorption resonance in the trace gases or chemical elements to be detected. A photodetector responds to the resulting radiation of fluorescent light caused by the laser induced biochemical fluorescence. As mentioned in the patent to Javan, it is also known to pulse the illuminating laser beam and gate the receiver coupled to the photodetector to cause it to respond in a delayed manner during a short period following each laser illumination pulse. The delay is fashioned to take advantage of the fluorescence decay time of the agent to be detected, so as to discriminate against false ambient illumination.

In addition to fluorescence techniques, particle geometry can be characterized by illuminating the particles with an excitation source and recording the scattering profiles. Such a system is described in U.S. Pat. No. 5,561,515 to Hairston et al.

Despite the availability of advanced apparatuses in the field of particle detection & classification, such as those described in the patents to Javan and Hairston et al., there is nevertheless a need for improved systems and methods.

SUMMARY OF THE INVENTION

In accordance with the present invention, a flow tube carrying a fluid is passed through a detector assembly. The detector assembly is configured such that the flow tube is surrounded by eight off-axis ellipsoidal mirrors, all having a common first focus coincident with a portion of the flow tube, and each having a distinct second focus. At one or more of the second foci there is coupled therethrough one or more sources of radiation, and in addition one or more high-gain optical sensors. In one embodiment all sources of energy are simultaneously energized, in an other embodiment selected sources are energized and in yet another embodiment each source (or groups thereof) is momentarily energized in sequence, causing light to illuminate (underfill) its corresponding ellipsoidal mirror. The light reflected from each mirror will strike the common first focus within a portion of the flow tube. Any particles suspended in the fluid and within the first focus will then scatter the light, and depending upon the source wavelength and the particle, may also provide some amount of fluorescence (either inherent to the particle or through fluorescent dye staining as is known in the art). This energy is captured by sensors coupled to each of the second foci for each of the eight mirrors, thereby defining, to at least a rough order, the scattering profile relative to the direction of the incident light from one of the ellipsoidal mirrors. The recorded energy distributions are then processed from all the mirrors in order to determine the type, size and quantity of particles at the first focus. The apparatus and method in accordance with the present invention also helps to determine if one particle is shadowing another.

The foregoing and other features of the present invention, along with the attendant advantages thereof, will be apparent to those skilled in the art upon reading the following detailed description in conjunction with the drawings.

DETAILED DESCRIPTION OF THE INVENTION

Figure 1:
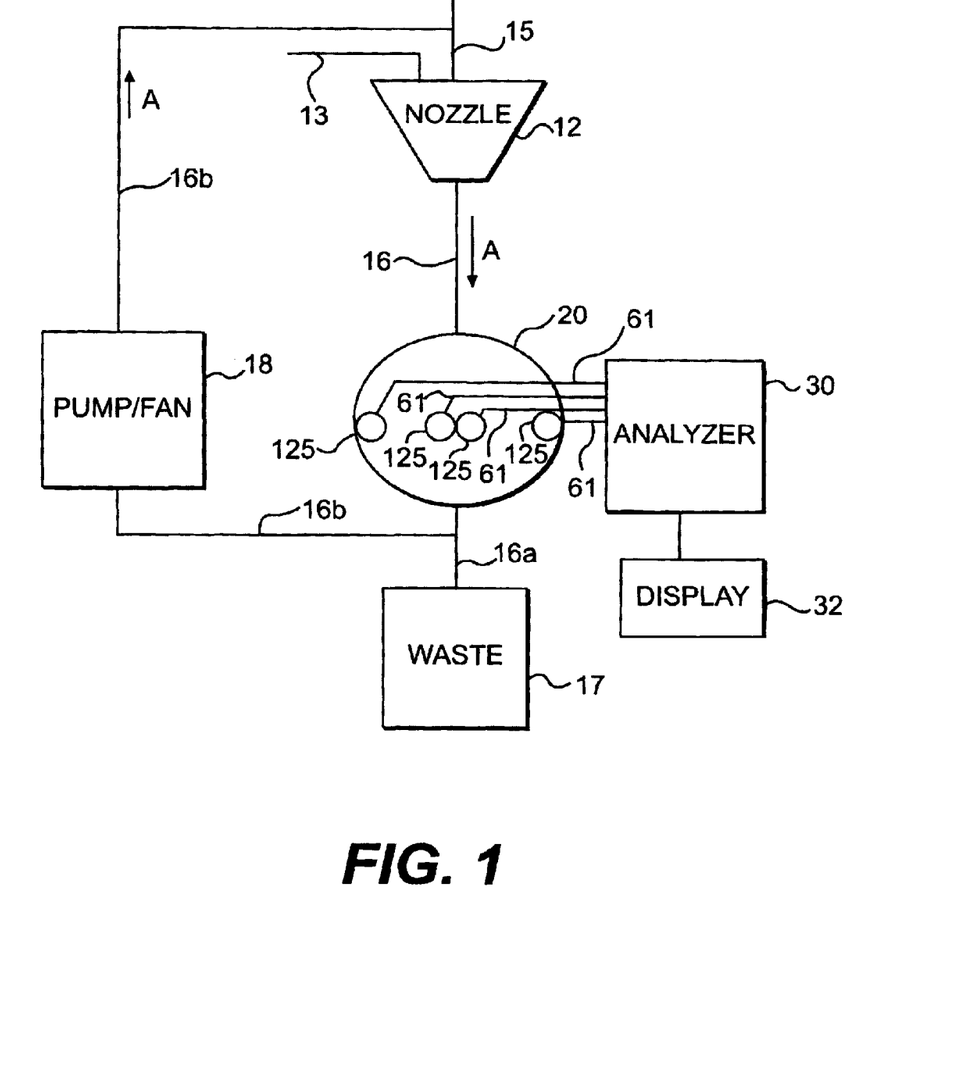
FIG. 1 is schematic representation of an exemplary system in accordance with the present invention.

FIG. 1 shows an exemplary component arrangement in accordance with the present invention including a nozzle 12 into which is provided a fluid with known properties by way of pipe 13. Particles to be detected are delivered to nozzle 12 through input tube 15. The fluid and the particles to be detected flow together, preferably such that the particles to be detected are distributed evenly throughout the fluid. Nozzle 12 is preferably arranged to generate droplets of the resulting fluid/particle mixture or to generate a stream of fluid with the particles to be detected suspended throughout. Nozzle 12 feeds flow tube 16, which is arranged to pass through detector assembly 20 (described in detail below). Flow tube 16 (or at least a portion thereof that passes through detector assembly 20) is preferably comprised of a transparent material (e.g., glass or plastic) with optical characteristics that do not inhibit or detrimentally effect light detection and reflection in accordance with principles of the present invention that are described later herein.

Those skilled in the art will appreciate that the "fluid" provided through pipe 13 in the context of the present invention includes both liquids and/or gases. Also, to the extent that the addition of a fluid through pipe 13 is unnecessary (e.g., when the particles to be detected are already suspended in a gas, or it is a gas itself that is to be detected), then nozzle 12 and pipe 13 may be eliminated altogether.

After passing through detector assembly 20, material in flow tube 16 is either passed as waste 17 through flow tube portion 16a, or is cycled through pump/fan unit 18 (the selection of a pump or fan depends, of course, on the nature of the material inside flow tube 16) through flow tube portion 16b, and back to an input end of flow tube 16. The general direction of fluid flow through the exemplary apparatus of FIG. 1 is shown by arrow A.

Also shown in FIG. 1 is an analyzer 30, which will be described later herein, and an optional display device 32, including one that might be connected to a general purpose computer (not shown) that is programmed to function in accordance with the principles of the present invention. Display 32 may also be, for example, a more simple LED or liquid crystal read out, or any other form of device that provides visual output to a user to indicate to the user the nature of the particles being detected.

Generally speaking, the particles to be detected are passed via flow tube 16 through detector assembly 20 wherein the particles to be detected are analyzed using one or more of several techniques that employ radiant energy, typically in the form of ultra violet radiation, laser light and/or non-collimated or non-coherent light.

FIGS. 2A, 2B, 2C and 2D illustrate a basic structure for an exemplary detector assembly 20 in accordance with the present invention. A similar structure, albeit used for an entirely different purpose, is described in detail in U.S. Pat. No. 6,428,198 B1, which is incorporated herein in its entirety. At a high level, detector assembly 20 is designed to receive a source (or sources) of radiant energy that is directed towards flow tube 16, which preferably passes substantially through a central longitudinal axis of detector assembly 20. Resulting reflected light and fluorescence effects are thereafter monitored via a plurality of detectors that are positioned at exit ports and that are connected, via optical fibers or lightguides 61, to analyzer 30 as shown in FIG. 1. In one preferable implementation, detector assembly 20 is approximately 3" by 4" by 3.6" high and comprises a plurality of ellipsoidal mirrors 10.

Figure 2A:
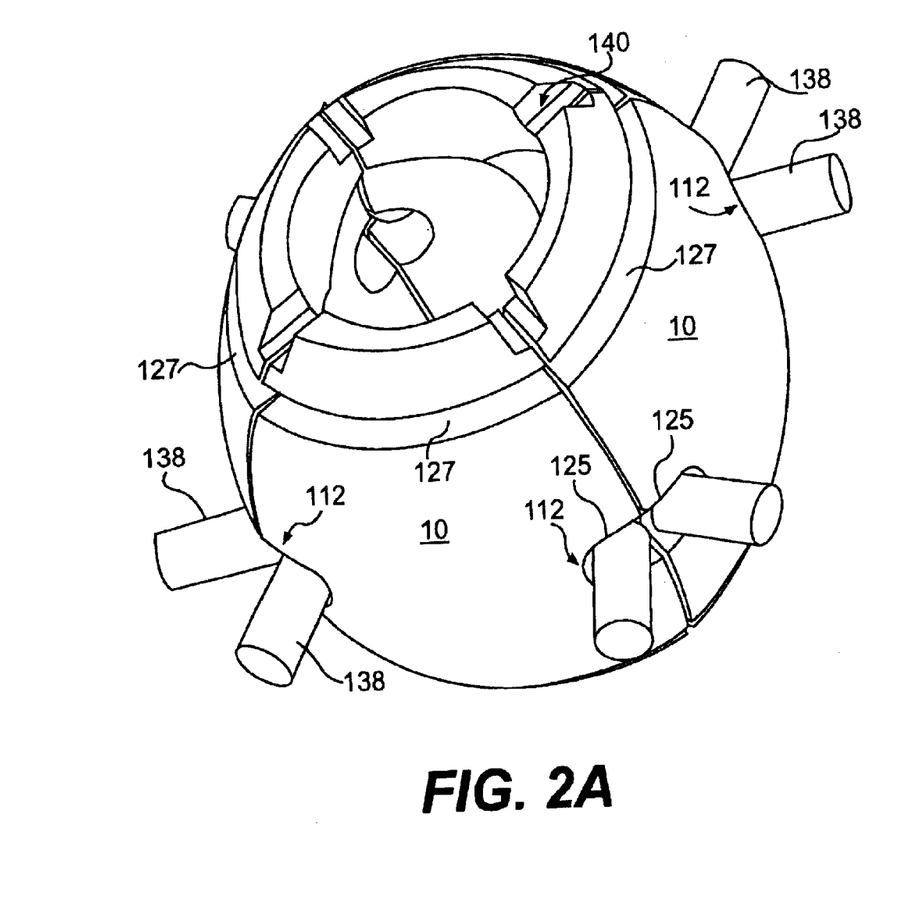
FIGS. 2A, 2B, 2C and 2D are, respectively, assembly, isometric and side elevation views of the exemplary detector assembly in accordance with the present invention.
Figure 2B:
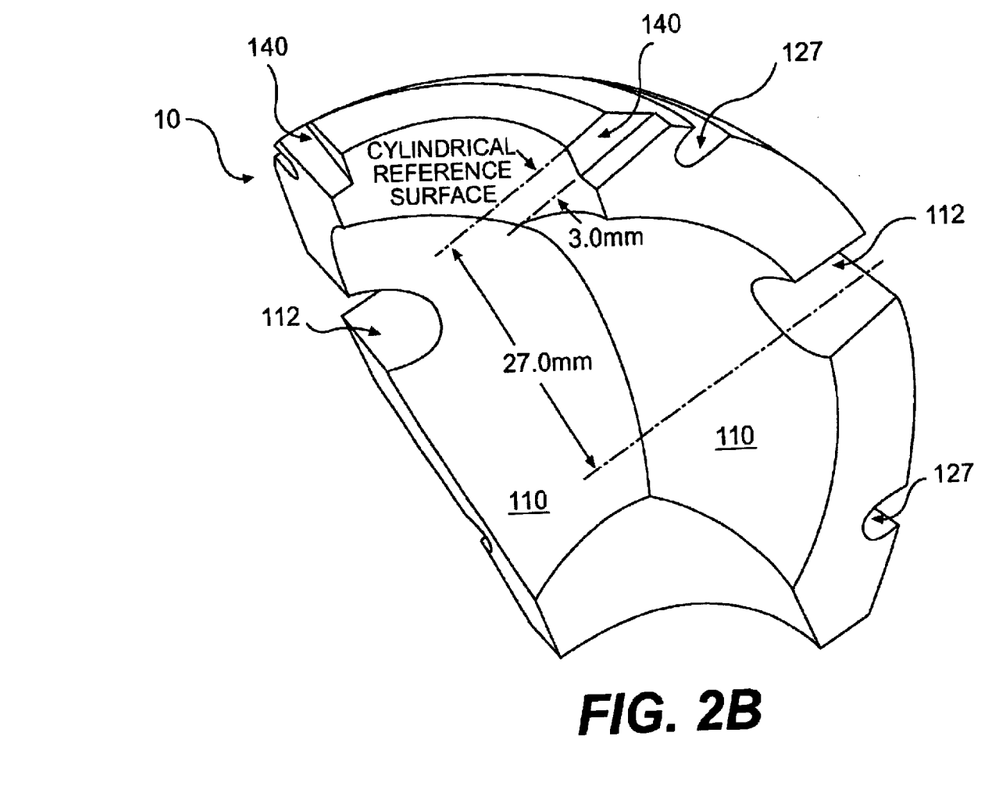
Figure 2C:
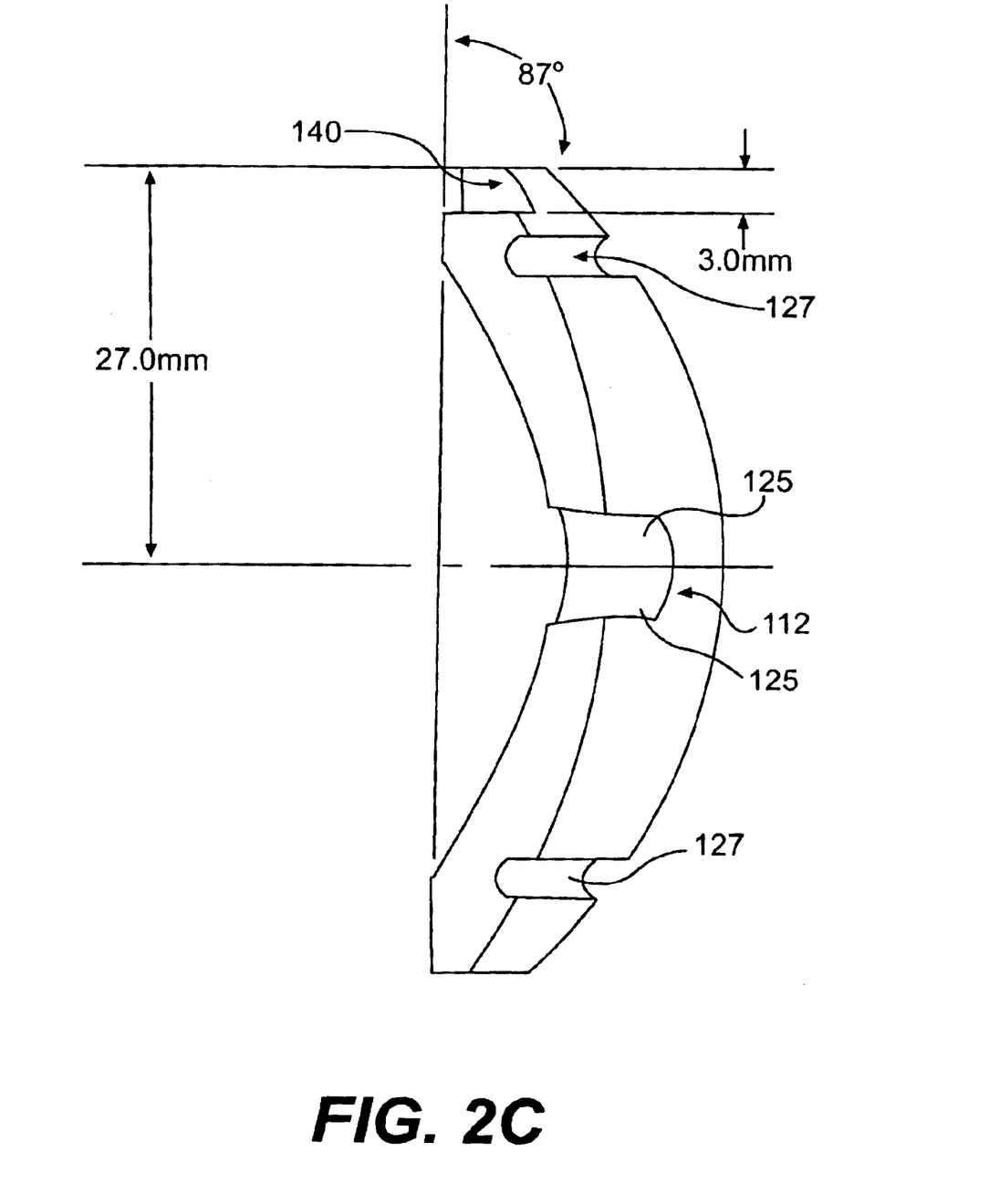
Figure 2D:
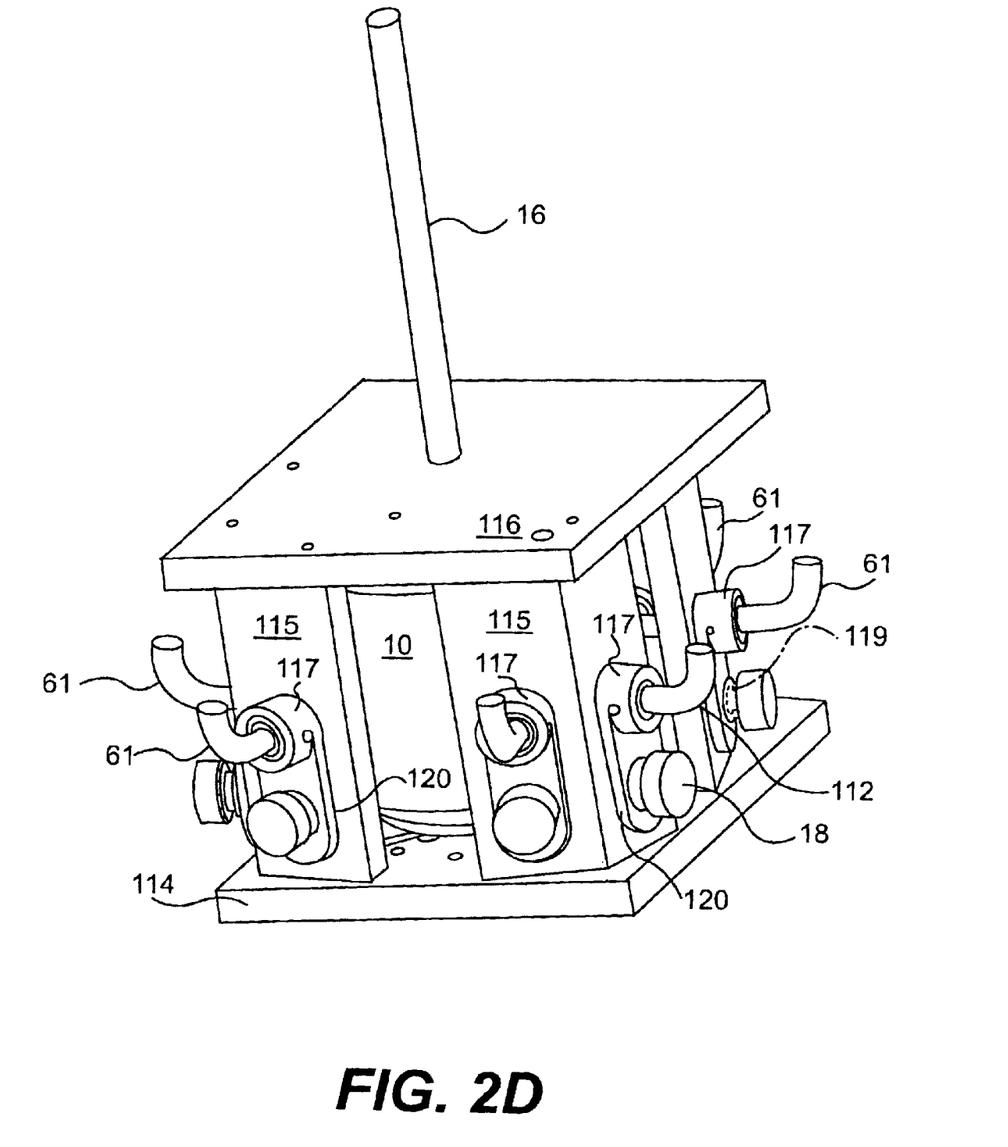

Ellipsoidal mirrors 10 are supported by a plurality of L-shaped support brackets 115. Each wing of the "L" is approximately 0.9" wide and 2.25" high. The isometric view of FIG. 2D shows three L-shaped support brackets 115, with the fourth one hidden behind detector assembly 20 in that view. Each bracket 115 preferably has a pair of clearance through-holes (one on each side of the "L") 117, to which lightguides 61 can be connected, and a pair of tapped holes 119 for securing each lightguide 61 to its respective adjuster 120 by means of thumb screw clamp 18. Through-hole 117 is approximately 0.36" in diameter and tapped hole 119 is approximately 0.19" in diameter. Ellipsoidal mirrors 10 are preferably supported by top and bottom hub plates 116, 114 each having approximate dimensions of 3" by 3.9" by 0.25" thick and having a diameter of 4.93". The height from the top of top hub plate 116 to the bottom of bottom hub plate 114, when supporting mirrors 10, is approximately 2.75".

To ensure that ellipsoidal mirrors 10 and mirror edge slots 112, which form exit port holes for detector assembly 20, are properly aligned, it is desirable (but not essential) to build a suitable set of accurate datum surfaces into the design of the assembly. Efficient light transmission and extraction can depend on such proper alignment. Details of possible datum surfaces are described in detail in U.S. Pat. No. 6,428,198 B1 and may be employed to the extent desired.

Referring still to FIGS. 2A–D, the top and bottom of the four ellipsoidal mirrors 10 preferably have cylindrical surfaces that engage cylindrical hubs of hub plates 116 and 114, respectively. In a preferred implementation, ellipsoidal mirrors 10 are securely held against hub plates 114 and 116 by means of garter springs (not shown, but see U.S. Pat. No. 6,428,198 B1) that engage matching torroidal grooves 127 ground into the backs of ellipsoidal mirrors 10.

Clocking alignment of each ellipsoidal mirror 10 about the hub axis is provided by notches 140 in the top corner edges of each mirror section. Notches 140 preferably have accurate reference datum surfaces that are normal to the bottom face of hub plate 116. The four L-shaped support brackets 115 and their eight through-holes 117 are accurately positioned with respect to the hub plate 116 so as to ensure proper alignment of through-holes 117 with mirror edge slots 112. Thus, as can be readily gleaned from FIGS. 2A–D (and other figures), the mirrors 10 (and mirror section 110 described below) are arranged along a circumference of a circle, which is coaxial with detector assembly 20, whose center is penetrated by flow tube 16 such that the mirrors (10, 110) surround flow tube 16.

In regard to fabrication, the unit cost of molding accurate glass surfaces is less than the cost of grinding them (and, of course, less than the cost of grinding and polishing them). Therefore, the critical surfaces of ellipsoidal mirrors 10 are preferably molded.

Each ellipsoidal mirror 10 comprises two ellipsoidal mirror sections 110, which is a preferable configuration for ease of manufacture. In a preferred implementation, each ellipsoidal mirror section 110 is positioned in such a way so as to have a first focal point common to all eight mirror sections 110, namely substantially centered on flow tube 16. Further, each ellipsoidal mirror section 110 preferably has a second unique focal point, each of which is substantially centered on or near a respective mirror edge slot 112 that provides a cylindrical exit port 125 for a corresponding cylindrical rod 138 (to be described in detail below). Thus, each ellipsoidal mirror section 110 focuses reflected light from flow tube 16 on a corresponding exit port 125 located at or near the second focal point of a given mirror section 110. Note that each mirror edge slot 112 is aligned with a respective L bracket port through hole 117. Each exit port 125 is on the order of, e.g., 4 mm in diameter. Note that the aforementioned dimensional characteristics are based upon a flow tube 16 having an inside diameter of about 1.5 mm.

There are preferably eight mirror edge slots 112 (one for each ellipsoidal mirror section 110) and thus eight corresponding clearance through-holes 117. Note that each mirror edge slot 112 is formed by a half-hole in a mirror edge. Each ellipsoidal mirror section 110 preferably has two half-holes, one on each side, thus providing four holes 112 and eight positions for cylindrical rods 138. In some implementations it may be desirable to enlarge the diameters of each cylindrical rod 138 to capture more reflected light. However, such enlargement typically requires a corresponding enlargement of each mirror edge slot 112, which reduces the area of the ellipsoidal mirror section 110 surfaces which, in turn, can actually reduce light collection efficiency. The efficiency loss attributable to this reduction in mirror area is significant when, e.g., the mirror edge slot 112 area is large enough to become a significant fraction of the mirror section 110 area. Note that detector assembly 20 can be scaled in size around the desired diameter of flow tube 16. The scaling is based upon the optical magnification of the design, which is on the order of 2.3, visually evident by the ratio of the length of the light rays shown in FIG. 4. Therefore, a larger diameter flow tube will generate a larger image at the second focus, thereby requiring a larger mirror edge slot. In order to maintain a high degree of collection efficiency for light scattered from the flow tube, the slot area should be small in relationship to the area of the ellipsoidal mirror surface, and therein lies the desire to scale the design in relation to the diameter of the flow tube. Such tradeoffs to maximize S/N can be optimized, in part, through use of optical simulation software such as ASAP manufactured by Breault Research Organization (Tucson, Ariz.).

While the illustrated detector assembly 20 design comprises four ellipsoidal mirrors 10 formed from eight ellipsoidal mirror sections 110, other alternative design configurations are contemplated by the present invention. For example, detector assembly 20 could comprise a greater or a lesser number of ellipsoidal mirrors disposed about flow tube 16 that would all have a common first focal point. As in the illustrated configuration, the second focal point of each mirror would preferably be unique and would be paired with a corresponding unique exit port for light egress. The greater the number of mirrors in the detector assembly 20, the smaller would be the solid angle intercepted by each mirror as seen from flow tube 16 or from the corresponding exit port. This assumes, of course, that the mirrors surrounding flow tube 16 are all identical.

Ellipsoidal mirrors 10 may be fabricated from materials such as metal, glass or plastic. Preferably the bulk materials do not exhibit fluorescence. Metal mirrors may be fabricated from, e.g., diamond-turned aluminum or electro-formed nickel. Glass mirrors can employ such materials as Schott B270 or Duran (borosilicate). Plastic mirrors can employ materials such as acrylic, polycarbonate or cycloolefin copolymer (COC) such as Topas from Ticona. Mirrors preferably use first-surface specular coatings such as aluminum, dielectric thin films, or other highly-reflective coatings of a non-fluorescing nature. The coating preferably reflects both the LED/laser light (e.g. UV) and the scattered light (UV and fluorescence). The coating may also comprise notch filter characteristics as desired to increase S/N. An additional benefit of the first-surface coating is to preclude light from entering the bulk material, minimizing the potential for any residual fluorescence effects in the bulk material, should it exist. Of course the surface of edge slots 125 and inside surfaces of hub plates 114 and 116 are exposed to light scatter from flow tube 16, and must be considered for fluorescence properties as well.

An optical fiber, such as a solid core fiber lightguide 61, is connected to cooperate with a corresponding exit port 125. This can be accomplished with or without a cylindrical rod 138 (described below). The position of each fiber 61 may be adjusted by a respective adjuster 120 to ensure proper alignment with the exit port 125. Note that each adjuster 120 is aligned with a corresponding fiber adjustment through hole 117.

Cylindrical rods 138 may be fabricated from solid glass (e.g., LaSFN31) having a high refractive index or from fused silica having a low refractive index. An exemplary cylindrical rod 138 is 13 mm in length and 4 mm in diameter. Such a rod 138 provides an optically transmissive element or light pipe, which can be air-spaced or bonded to its corresponding fiber 61.

Note that each of mirror section 110 is an ellipsoid of revolution about the ellipsoid major axis. Accordingly, detector assembly 20 has eight ellipsoidal mirrors sections 110 having a first common focal point at the center of the assembly's cavity and a second unique focal point, not shared with any other ellipsoid, which is at one of the eight mirror edge slots 112 located near the edge of each adjacent ellipsoidal mirror section 110. The second focus is preferably located such that light rays reflecting from the ellipsoidal mirror avoid intersecting flow tube 16, again with the intent of maximizing S/N.

Mirror edge slots 112 can preferably interface with a respective transmissive element (e.g., element 51 shown in FIG. 3) or an optical light pipe such as solid cylindrical rod 138 or a rod that morphs from round to a polygonal shape over its length to efficiently couple to an equivalently shaped waveguide (e.g., element 51). Note that the second focus from ellipsoidal mirrors can be designed such that it lies beyond slots 125, thereby precluding the need for rods 138, for example, coupling directly from an ellipsoidal mirror to element 51. This would, however, require a slighty larger slot diameter to preclude shadowing by the ellipsoidal mirror surrounding the edge slots.

Figure 3:
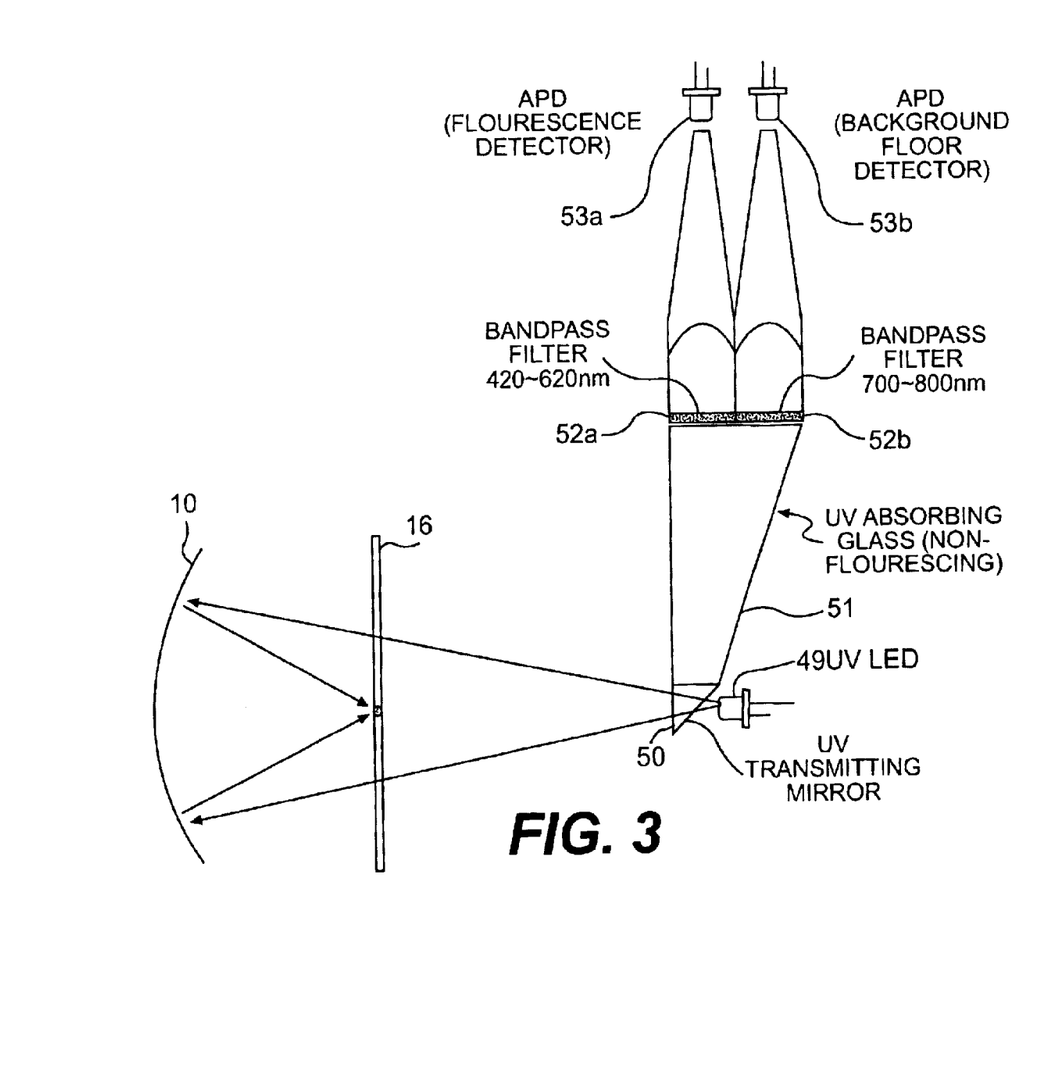
FIG. 3 illustrates an arrangement including a UV LED for exciting and detecting a sample in accordance with the present invention.

There are two primary ways to irradiate the substance flowing in flow tube 16 to achieve the desired fluorescent response from the particles to be detected. A first way is to have each (or at least a subset) of the exit ports 125 function as combined input and output ports. FIG. 3 shows an arrangement in which an ultra violet (UV) LED (laser diode, or a UV-carrying fiber from a remote source of UV) 49 is positioned on one side of a UV transmitting mirror 50 that is located adjacent at least one of the exit ports 125. The divergence of UV from the LED is preferably chosen to slightly underfill the opposing ellipsoidal mirror 10. The geometry of the ellipsoid mirrors 10 is design to substantially concentrate all of the UV light across the inside diameter of flow tube 16. Thus, as shown, radiation emitted by UV LED 49 is transmitted through UV transmitting element 50 and a particle to be detected in flow tube 16 is "illuminated". Upon this illumination, the particle to be detected may absorb the UV radiation thereby causing fluorescent light to be generated. This fluorescent light is then received at one or more of the exit ports 125, as a result of the unique locations of the focal points of the several ellipsoidal mirror sections 110 disposed around flow tube 16 in detector assembly 20. In a preferred embodiment, the generated (non-UV) fluorescent light thus falls on UV transmitting element 50 and is reflected up through a UV absorbing glass (non-fluorescing) trapezoidal waveguide 51. Preferably, one or more bandpass filters 52*a*, 52*b* are placed in line with waveguide 51 such that one or more photo detectors 53*a*, 53*b* (in this case avalanche photo detectors, APDs) can detect the appropriate band of radiation. Thus, according to the first primary way to irradiate the substance flowing in flow tube 16, exit ports 125 can be utilized as combination input and output channels via which UV radiation and returning fluorescent radiation is passed. It should be noted that this embodiment has been described with non-imaging optics arranged at exit ports 125. However, imaging optics could be utilized at one or more exit ports 125, as desired.

Advantages of the foregoing arrangement include the fact that the source need not contain additional optics, since the ellipsoidal mirror will focus the expanding UV beam onto flow tube 16 at a point (as shown in FIG. 3). Also, this arrangement allows detection of particles in shadow, especially in the case where a UV source is placed at more than one port. On the other hand, one disadvantage of this configuration is it complicates the assembly at each exit port 125.

Figure 4:
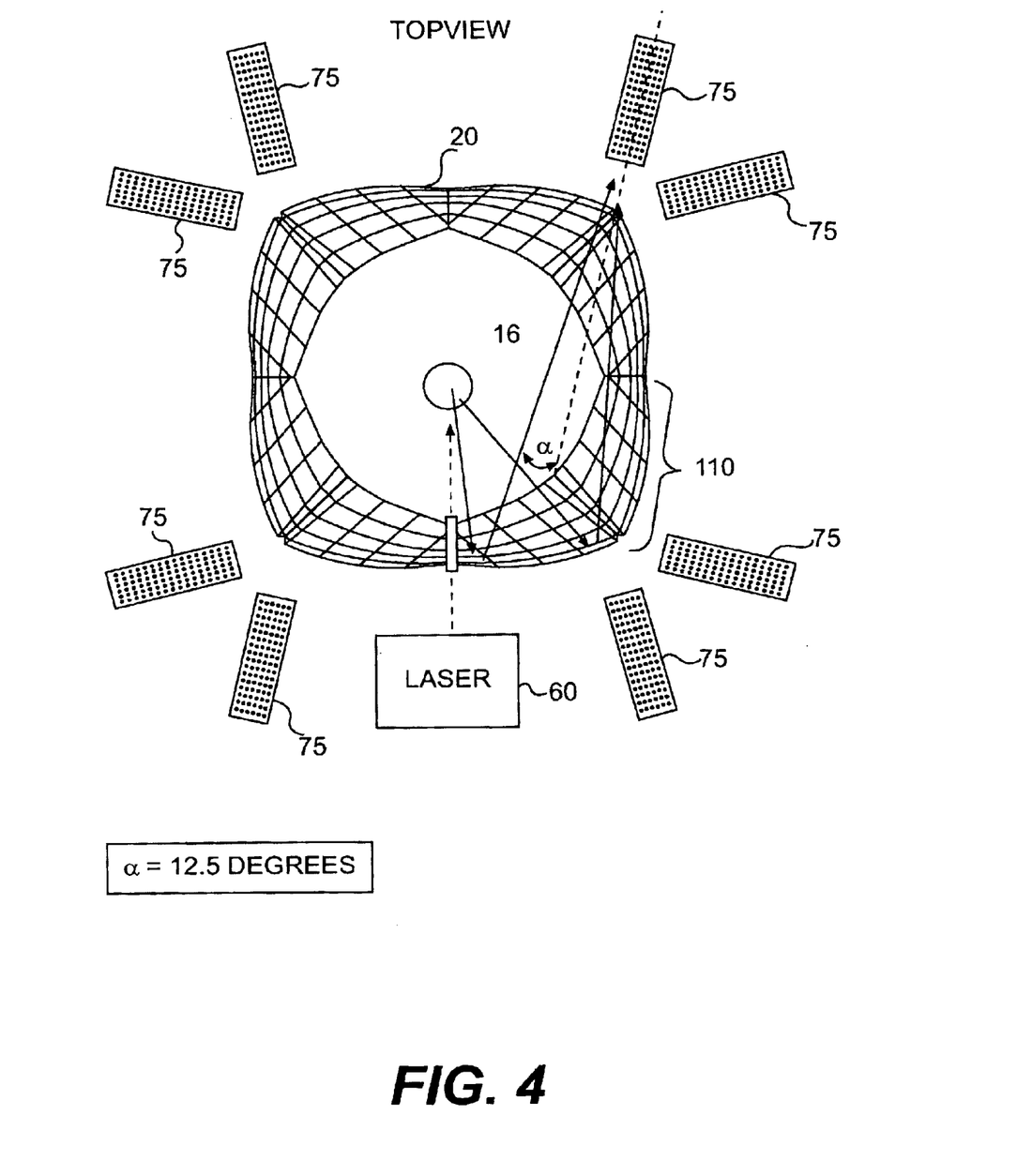
FIG. 4 illustrates a detector assembly having a laser excitation source, in accordance with the present invention.

In accordance with a second primary way to irradiate the substance flowing in flow tube 16, a laser 60 (shown in FIG. 4) is employed. While this laser could be arranged to be co-located with the individual detecting apparatus arranged at each exit port 125, it is also possible to locate the laser (or other excitation source that has a small beam width and that is collimated) at a separately provided aperture placed into one or more mirror sections 110. This latter configuration is depicted in FIG. 4. Those skilled in the art will appreciate that in the eight mirror version of the present invention described herein different combinations of sources and detectors can be employed.

Advantages of this second implementation include avoiding consuming any of the eight port locations for the excitation source and allowing each exit port 125 to have the same configuration of detectors (e.g., a trapezoidal waveguide or an imaging optic).

Some possible disadvantage of such an arrangement include the fact that the source possibly needs to have additional optics to collimate the beam, and may require appropriate alignment structure to ensure it irradiates flow tube 16. Also, the beam size needs to be small enough to avoid consuming a large fraction of the ellipsoidal mirror surface(s), which would result in lower sensitivity for those ports whose associated mirrors have holes in them. A small beam is also desirable so that it only irradiates a small portion of flow tube 16 so as to minimize the number of particles it illuminates. Also, a single laser may not be able to illuminate some particles that are being shadowed by other particles.

Figure 5:
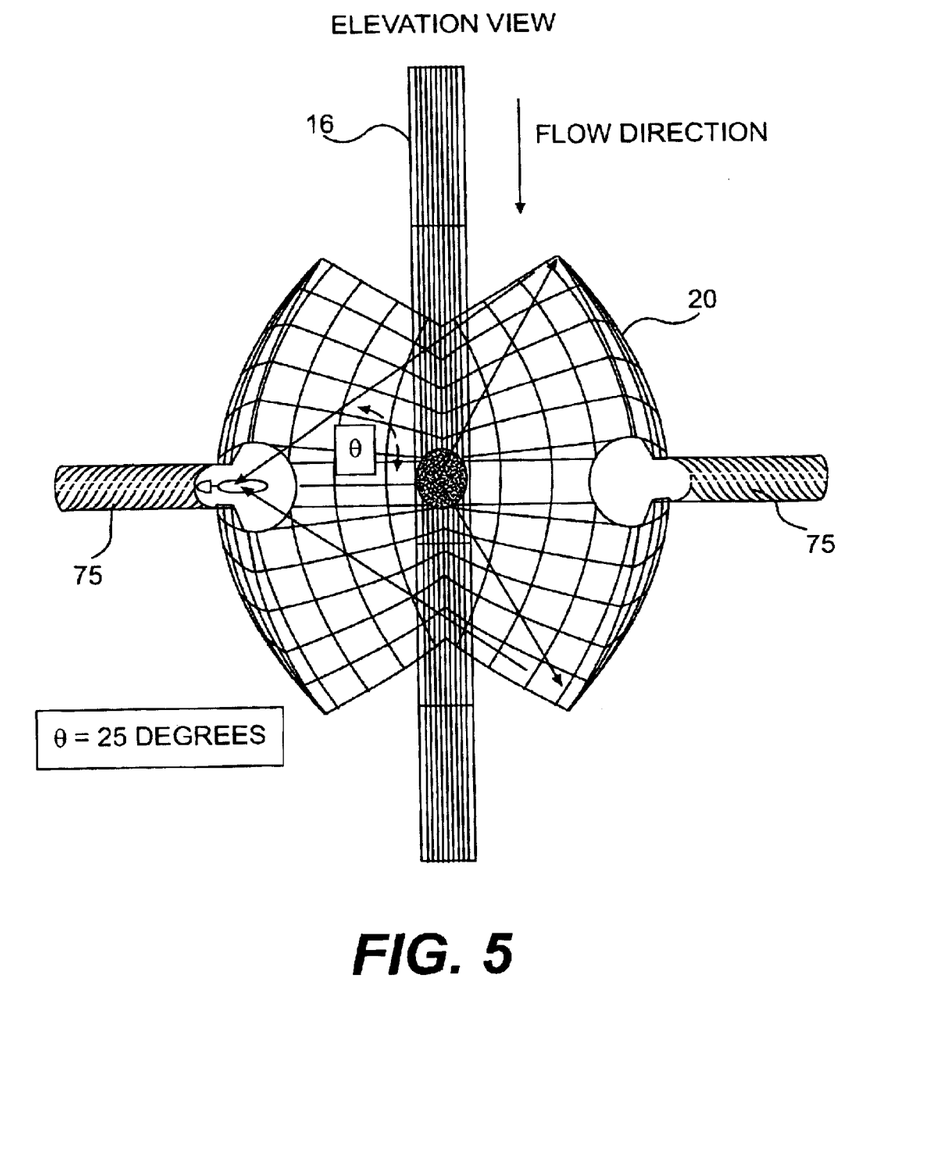
FIG. 5 depicts an elevation view of an embodiment of the present invention.

FIG. 4 and FIG. 5 show respectively top and elevation views of an embodiment of the present invention. These figures illustrate, with the several illustrated ray traces, how light that is scattered by a particle in flow tube 16 is collected at a selected imaging and/or non-imaging detector 75. An imaging detector might be, for example, a pixellated array such as intensified CCDs, whereas a non-imaging detector is intended to include devices such as photo diodes, like those shown in FIG. 3, or simply transmissive device such as trapezoidal waveguide 51.

In the case of FIG. 4, an angle α (alpha) is presented and in the case of FIG. 5 an angle θ (theta) is presented. These angles represent the collection half-angles in azimuth (alpha) and elevation (theta) for the sectional views of these figures. If we assume that a particle fluoresces after being irradiated, and further assuming the fluorescence is isotropic (equal energy radiating per solid angle), a detector placed at the second focus of each ellipsoidal mirror section 110 would receive light from all points of the mirror. Since the mirror is asymmetric, the converging beam is also asymmetric, and can be represented (roughly) by maximum collection half-angles of alpha and theta. In reality, as shown in FIG. 2B, the boundary of each mirror section 110 is somewhat complex, and so, for example, fluorescent light striking a mirror section 110 at the uppermost and lowermost corners of the mirror might exceed alpha and beta. Note that the trapezoidal optic 51 shown in FIG. 3 is used to collimate theta from +/−25 degrees to be equivalent to alpha at +/−12.5 degrees, while leaving alpha unchanged.

Figure 6:
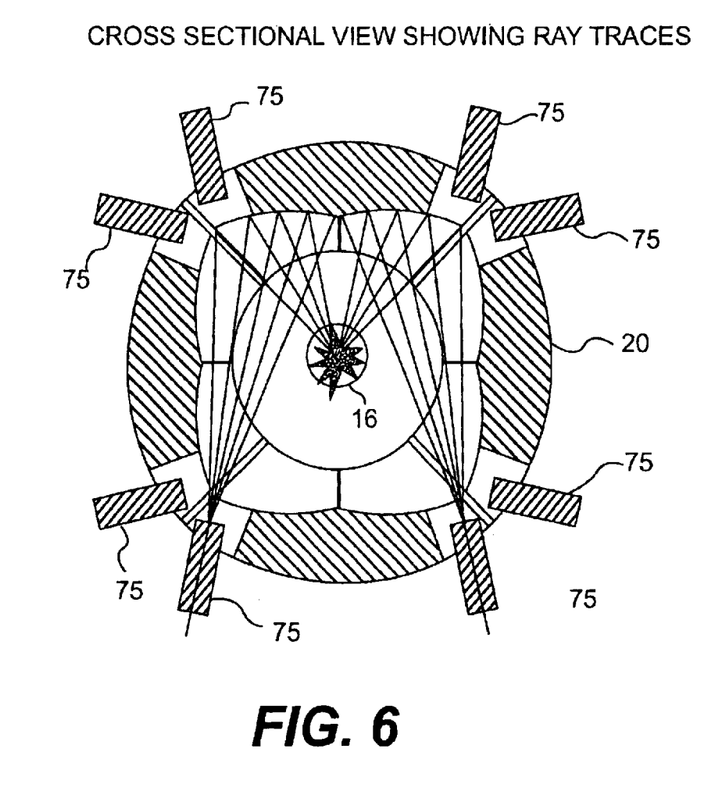
FIG. 6 illustrates a cross sectional view of the detector assembly, including ray traces, in accordance with the present invention.

FIG. 6 shows yet another cross sectional top view of detector assembly 20 with several exemplary ray traces. As shown, flow tube 16 is positioned at a common first focus of all eight ellipsoidal mirror sections 110. Each ellipsoidal mirror section 110 also has a distinct second focus, mainly on one of the exit ports 125. Consequently, reflected light beams miss flow tube 16 thereby achieving high collection efficiency at exit ports 125.

Although it should be apparent to those skilled in the art, it is nevertheless noted that each detector 75 mounted adjacent an exit port 125 detects light that arrives from a predetermined one of the corresponding ellipsoidal mirror sections 110.

Referring to FIG. 3, it should be understood by those skilled in the art that one or more ports 125 can be equipped with these devices. Specifically, a trapezoidal non-imaging optic 51 (with appropriate bandpass filters, if so desired) is provided at the output of an exit port 125. Such an optic device (which can be fabricated by Mindrum Precision, Rancho Cucamonga, Calif.) can make the asymmetric angular output (+/−12.5 degrees, +/−25 degrees) to be symmetric as previously explained. Alternatively, the asymmetry can be advantageous when trying to couple laser light through one or more ports into detector assembly 20, since most laser diodes have asymmetric angular spreads. It is also important to note that if particle geometry is the primary desire (and not biodetection via fluorescence), then UV LED 49 (e.g., available from Roithner Lasertechnik, Vienna, Austria) can be replaced by a non-UV light source, of which there are numerous sources know to those skilled in the art. Further, APD 53b can be replaced with the source, and APD 53a can employ two or more detectors in the same device to provide enhanced S/N (e.g. to subtract dark noise) as is known in the art and described in Photodiode Amplifiers, Op Amp Solutions, J. Graeme, McGraw-Hill, ISBN 0-07-024247-X. APDs are available in custom arrays from Pacific Sensors, (Westlake Village. Calif.). Suitable bandpass filter technology, having very high transmittance and extinction ratios can be obtained from Omega Optical, Inc., (Brattleboro, Vt.). Also note that the spectral transmittance of elements shown in FIG. 3 are selected to enhance the S/N based on the wavelengths of interest in such a design. Such materials can be obtained for example, from Schott Glass Technologies, Inc. (Duryea, Pa.).

In a preferred embodiment, an intensified CCD (e.g. from Hamamatsu, see http://usa.hamamatsu.com/sys-applications/fluorescence.htrnl), or like imaging device, receives light at-or-projected-from the second focus of an ellipsoid, and which may be electronically captured such that it can be displayed on a display 32 and/or saved and/or manipulated electronically with analyzer 30, or more generally, a computer (as is well-known in the prior art).

In view of the configuration of detector assembly 20, the present invention offers several unique advantages in the art of particle detection. For example, the configuration of the detector assembly 20 in accordance with the present invention is much more compact and by substantially (or even completely) surrounding the flow tube with collection mirrors, much higher in collection efficiency than conventional particle detectors. Further, the method of irradiating the particles in the round or in a sequential rotary fashions offers another dimension of functionality.

More specifically, as described above, flow tube 16 is surrounded by eight off-axis ellipsoidal mirrors, all having a common first focus coincident with a portion of flow tube 16, and each having a distinct second focus. At some or all of the second foci, namely exit ports 125, there is placed one or more sources of radiation, and in addition, one or more high-gain optical sensors, e.g., detectors 75. In the separately-located laser source embodiment, the source of radiation may be co-located with exit ports 125 or separately located.

Each source is momentarily and simultaneously energized, energized in groups (e.g., for irradiation from orthognal directions), or momentarily energized in sequence, causing light to illuminate (underfill) its corresponding ellipsoidal mirror section 110. This light strikes the common first focus within a portion of flow tube 16. Any particles within the first focus will then scatter the light, and depending upon the source wavelength and the particle, may also provide some amount of fluorescence. This energy is captured by detectors 75 at each of the second foci, exit ports 125, for each of the eight mirrors, thereby defining, to at least a rough order, the scattering profile relative to the direction of the incident light from one of the ellipsoidal mirrors. The recorded energy distributions are then processed from all the mirrors in order to determine the type, size and quantity of particles at the first focus. This method of analysis "in the round" also helps to determine if one particle is shadowing another.

In the case of UV LEDs 49 that may not be fast enough or if the fluorescence decay times are long (when compared to the velocity of the particles in flow tube 16) then the pulsing sequence can be arranged so that flow tube 16 is irradiated at orthogonal views closest-in-time, which would give the best opportunity to discern whether one or more particles is being shadowed. It may also be desirable to pulse all the UV LEDs at the same during at least each recurring measurement cycle time to maximize signal-to-noise for at least one measurement.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents. For example, the excitation source can be coupled into the flow tube along the direction of particle flow, using the tube as a light pipe, with one or more extraction features adjacent to the common first foci. Also, alternate collection optic geometries can be employed that fully surround the flow tube, such as ones that include curved or multi-faceted mirrors, ones that include various arrangements of distribution arrays, as well as arrangements such as those described in U.S. Pat. No. 6,428,198.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. An apparatus for detecting particles, comprising:
    a passage through which particles to be detected travel;
    a detector assembly through which the passage passes; and
    an analyzer in communication with the detector assembly,
    wherein the detector assembly comprises at least one excitation source and a plurality of off-axis ellipsoidal mirrors all having a common first focus coincident with a portion of the passage and each having a distinct second focus, each of the mirrors being arranged along a circumference of a circle whose center is penetrated by the passage such that the mirrors surround the passage.

2. The apparatus of claim 1, wherein the passage comprises a flow tube.

3. The apparatus of claim 1, wherein the detector assembly further comprises exit ports that are arranged to coincide respectively with a distinct second focus.

4. The apparatus of claim 1, wherein the detector assembly further comprises a plurality of exit ports, wherein a total number of exit ports equals a total number of ellipsoidal mirrors.

5. The apparatus of claim 4, wherein the excitation source comprises at least one of a laser and an ultraviolet light emitting diode.

6. The apparatus of claim 5, wherein the excitation source is arranged to be co-located with an exit port.

7. The apparatus of claim 5, wherein the excitation source is located at a location different from any of the exit ports.

8. The apparatus of claim 1, further comprising a display in communication with the analyzer.

9. The apparatus of claim 1, further comprising a nozzle through which the particles to be detected pass.

10. The apparatus of claim 1, wherein the detector assembly comprises eight ellipsoidal mirrors sections.

11. The apparatus of claim 1, wherein the detector assembly comprises four mirror components, each comprising two ellipsoidal mirror sections.

12. The apparatus of claim 1, further comprising at least one non-imaging detector.

13. The apparatus of claim 1, further comprising at least one imaging detector.

14. The apparatus of claim 1, wherein the detector assembly is comprised of four molded parts.

15. The apparatus of claim 1, further comprising a non-imaging device connected between the detector assembly and analyzer, the non-imaging device including at least one bandpass filter.

16. An apparatus for detecting particles by observing fluorescent radiation, comprising:
    eight ellipsoidal mirrors surrounding a flow tube through which particles to be detected travel, all of the mirrors having a common first focus coincident with a portion of the flow tube, and each having a distinct second focus on a respective exit port at which is arranged at least one optical sensor; and
    at least one excitation source,
    wherein when the excitation source irradiates the portion of the flow tube with particles traveling therein radiant energy generated by such particles is focused on the respective exit ports that surround the flow tube.

17. The apparatus of claim 16, wherein the at least one excitation source transmits energy through an exit port.

18. The apparatus of claim 17, wherein the excitation source transmits UV light.

19. The apparatus of claim 16, wherein the at least one excitation source transmits energy towards the flow tube from a location other than an exit port.

20. The apparatus of claim 19, wherein the excitation source comprises a laser.

21. The apparatus of claim 16, at least one detector that detects radiant energy at each exit port.

22. The apparatus of claim 16, further comprising a display for providing information to a user about the nature of the particles to be detected.

23. The apparatus of claim 16, wherein the ellipsoidal mirrors are arranged in four molded parts.

24. The apparatus of claim 16, further comprising a non-imaging device connected to at least one exit port, the non-imaging device including at least one bandpass filter.

25. A method of detecting particles, comprising the steps of:
    passing a fluid containing particles to be detected past a plurality of off-axis ellipsoidal mirrors that surround in a substantially circular fashion a passage through which the fluid passes, the ellipsoidal mirrors all having a common first focus and each having a distinct second focus that is coincident with an exit port through respective ellipsoidal mirrors;

momentarily energizing a plurality of excitation sources surrounding the passage thereby causing light to illuminate a corresponding ellipsoidal mirror and thereby irradiate the fluid at the common first focus;

detecting scattering and fluorescence energy generated by the particles; and processing the scattering and fluorescence energy and determining at least one of a type, a size and a quantity of the particles at the common first focus.

26. The method of claim 25, further comprising passing the fluid through a flow tube.

27. The method of claim 25, wherein the excitation sources comprise lasers.

28. The method of claim 25, wherein the excitation sources comprise UV light sources.

29. The method of claim 25, wherein each excitation source is coincident with a respective exit port.

30. The method of claim 25, further comprising recording the detected scattering and fluorescence energy.

31. The method of claim 25, wherein the step of detecting comprises passing scattered light and fluorescence energy through a non-imaging device having at least one bandpass filter.

32. A method of detecting particles, comprising the steps of:

arranging a plurality of off-axis ellipsoidal mirrors around a fluid passageway, all of the mirrors having a common first focus coincident with a portion of the fluid passageway, and each having a distinct second focus coincident with a distinct exit port;

co-locating a plurality of radiation sources at at least two of the exit ports;

causing a fluid to be passed through the fluid passageway;

momentarily energizing in sequence the radiation sources thereby causing light to illuminate a corresponding mirror and thereby irradiate the fluid in the fluid passageway;

detecting scattering and fluorescence energy generated by at least one of the fluid and particles within the fluid; and processing the scattering and fluorescence energy and determining at least one of a type, a size and a quantity of particles being carried by the fluid.

33. The method of claim 32, wherein eight mirrors are arranged to surround the fluid passageway.

34. The method of claim 32, wherein the radiation sources comprise lasers.

35. The method of claim 32, wherein the radiation sources comprise UV light sources.

36. The method of claim 32, further comprising recording the detected scattering and fluorescence energy.

37. The method of claim 32, wherein the step of detecting comprises passing scattered light and fluorescence energy through a non-imaging device having at least one bandpass filter.

* * * * *